United States Patent [19]

Leuker et al.

[11] Patent Number: 4,640,121
[45] Date of Patent: Feb. 3, 1987

[54] METHOD FOR FINDING A LEAK IN PRESSURE-CARRYING VESSELS AND APPARATUS FOR CARRYING OUT THE METHOD

[75] Inventors: Wilhelm Leuker, Gosberg; Günter Stipsits, Neunkirchen/Brand; Bernhard Thiel, Forchheim, all of Fed. Rep. of Germany

[73] Assignee: Kraftwerk Union Aktiengesellschaft, Mülheim, Fed. Rep. of Germany

[21] Appl. No.: 655,864

[22] Filed: Sep. 28, 1984

[30] Foreign Application Priority Data

Oct. 5, 1983 [DE] Fed. Rep. of Germany ....... 3336245

[51] Int. Cl.$^4$ .............................................. G01M 3/24
[52] U.S. Cl. .................................. 73/40.5 A; 340/605
[58] Field of Search ........................... 73/40.5 A, 592; 340/605

[56] References Cited

U.S. PATENT DOCUMENTS 3,713,127 1/1973 Keledy et al. .
4,289,019 9/1981 Claytor .......................... 73/40.5 A
4,457,163 7/1984 Jäckle ............................ 73/40.5 A

FOREIGN PATENT DOCUMENTS 2848702 5/1979 Fed. Rep. of Germany .
87835 7/1981 Japan ............................... 73/40.5 A
953479 8/1982 U.S.S.R. ............................. 73/592

Primary Examiner—Stewart J. Levy
Assistant Examiner—Joseph W. Roskos
Attorney, Agent, or Firm—Herbert L. Lerner; Laurence A. Greenberg

[57] ABSTRACT

A method for determining the location of a leak in pressure-carrying vessels, including a plurality of probes spaced-apart on walls of the vessels for picking up high-frequency solid-conducted sound noises, and an amplifier connected to the probes, includes forming an r.m.s. value in the amplifier from the sound noises, comparing the r.m.s. value with a threshold value, issuing a signal if the r.m.s. value exceeds the threshold value, comparing the solid-conducted sound noises from at least two probes with each other for localizing the leak, placing the r.m.s. values of the solid-conducted sound noises in a relationship relative to the spacing between the probes based on the comparison, and determining the location of the leak as the location of the maximum solid-conducted sound noise from the relationship.

18 Claims, 5 Drawing Figures

METHOD FOR FINDING A LEAK IN PRESSURE-CARRYING VESSELS AND APPARATUS FOR CARRYING OUT THE METHOD

The invention relates to a method for determining the location of a leak in pressure-carrying vessels, including several probes which which are disposed on walls of the vessel and pick up high-frequency sound noises, from which an r.m.s. value is formed by means of an amplifier, the r.m.s. value being compared with a threshold and a signal being given if the threshold value is exceeded. The invention also relates to an apparatus particularly well suited therefor.

In order to carry out a method known from German Published, Non-Prosecuted Application DE-OS 28 48 702, several probes are disposed at the reactor loop of a pressurized-water reactor. The probes only serve to indicate the presence of a leak per se, so that it is accordingly still necessary to determine the location of the leak by conventional methods, such as by an inspection performed by the operating personnel. This can take a great deal of time and can lead to a situation wherein more leakage occurs before the location of the leak is determined.

It is accordingly an object of the invention to provide a method and device for finding a leak in pressure-carrying vessels, which overcomes the hereinafore-mentioned disadvantages of the heretoforeknown methods and devices of this general type, and to determine the location of the leak quickly and reliably.

With the foregoing and other objects in view there is provided, in accordance with the invention, a method for determining the location of a leak in pressure-carrying vessels, including a plurality of probes spaced-apart on walls of the vessels for picking up high-frequency solid-conducted sound noises, i.e. those conducted through solids, and an amplifier connected to the probes, which comprises forming an r.m.s. value in the amplifier from the sound noises, comparing the r.m.s. value with a threshold value, issuing a signal if the r.m.s. value exceeds the threshold value, comparing the solid-conducted sound noises from at least two probes with each other for localizing the leak, placing the r.m.s. values of the solid-conducted sound noises in a relationship relative to the spacing between the probes based on the comparison, and determining the location of the leak as the location of the maximum solid-conducted sound noise from the relationship.

The localization of the leak according to the invention is based on the fact that the bulk or solid-conducted sound noises are subject to attenuation in their propagation from the leak over the walls of the vessel. The attenuation is frequency-dependent. The attenuation can be brought into a relationship to the spacing between the probes, especially if a micro-computer is used. The location of the maximum noise at which the sound source, i.e., the leak, must be located, can be determined therefrom. Practical tests have shown that the location of leaks can be determined accurately to within a few percent of the distance between the probes.

In accordance with another mode of the invention, there is provided a method which comprises digitizing the solid-conducted sound noises for the comparison. This facilitates the further processing by microcomputers; in principle, however, processing of analog values is also possible.

In accordance with a further mode of the invention, there is provided a method which comprises determining the solid-conducted sound noises by comparing with a background noise averaged over at least ten minutes. This permits particularly accurate localizations. Therefore, the absolute value of the solid-conducted sound noise is not determined, but rather its increase relative to the background noise which, in turn, is determined as a mean value. With such a mean value, the response level can be kept lower than if it were to be determined as an absolute value. In addition, data can be obtained in the determination of the mean value, which can be used to advantage for determining the leak as to size and location.

The meaning of the term "container" in connection with the invention is not only a tank with a simple spatial configuration in the usual sense, but also systems with piping inbetween such as belong to the coolant loop of a nuclear reactor, for instance. However, the invention can also relate to piping systems of chemical installations or the like.

In accordance with an added mode of the invention, there is provided a method which comprises interconnecting at least three probes of a vessel system through a ring line, and exciting two alarms through the ring line. In all systems, this is possible.

In accordance with an additional mode of the invention, there is provided a method which comprises carrying out the comparison separately for different frequencies, and averaging the location determined by the separate comparisons. This yields a particularly accurate evaluation. This is because the invention utilizes the fact that the attenuation of the bulk or solid-conducted sound in the vessel walls is frequency-dependent. Therefore, several localizations which permit a mutual correction when summed up, are obtained from a comparison of the attenuation for different frequencies.

In accordance with again another mode of the invention, there is provided a method which comprises comparing the comparison with a fixed upper threshold, a lower threshold and an upper sliding threshold. With these multiple comparisons, the invention even covers the case in which slow rises over an extended period of time are present, as opposed to the comparison known from German Published, Non-Prosecuted Application DE-OS 28 48 702, with an upper threshold. The lower threshold monitors the operability of the system.

In accordance with again a further mode of the invention, there is provided a method which comprises exciting the probes at defined time intervals with a given sound signal, and calibrating the probes by means of the excitation. In this way, changes in state of the sensitive probes are covered and equalized. The calibration can be made, for instance, once in 24 hours, especially if monitoring electronics are provided which perform such a calibration automatically. Correction factors are then assigned to the individual probes, through which their signals are multiplied in the subsequent evaluation.

In accordance with again an added mode of the invention, there is provided a method which comprises exciting the calibrated probes with a spatially defined sound signal, and localizing the point of excitation. In this way the agreement of the localization by the probes including the evaluation electronics is checked. The check can likewise be made, for instance, once every 24 hours. It is thereby also possible to locate failing probes so fast that the operating safety of the system is assured especially if the system includes a larger number of probes, so that redundancy is provided.

According to the invention it is important that the background noises are kept as low as possible.

In accordance with again an additional mode of the invention, there is provided a method including a main coolant pump of a nuclear reactor connected to the vessels, which comprises shutting off the main coolant pump during the determination of the solid-conducted sound noises. This is done because it permits the noise level to be reduced substantially so that the sensitivity is increased. Tests have shown that leakage rates of less than 30 kg/h can be detected with the increased sensitivity, while leakage rates of up to 100 kg/h could be determined with certainty while the pump was running. This applies particularly for nuclear reactors with several coolant loops, in which the reactor coolant pump in one loop can be shut off without causing detrimental effects on the operation.

In order to carry out the method there is provided an apparatus for determining the location of a leak in pressure-carrying vessels, comprising a plurality of probes with outputs including piezo-electric pickups spaced apart on walls of the vessels for picking up high-frequency solid-conducted sound noises, an amplifier connected to the probes for forming an r.m.s. value from the sound noises, a ring line interconnecting the outputs of the probes, and a head station connected to the ring line, the head station including at least one memory forming a long-term average.

Advantageously, the larger the vessels to be monitored, the larger the number of probes. Their spacing should not be substantially larger than about 10 m. Then, an accuracy of the leak localization of about 1 m is accomplished.

The memory for forming the long-term average is used for the sliding threshold, which defines the margin from the operating noise that may change. The memory may also serve to document the "history" in the event of a leak or a change in the leak noise.

The leak noises can be processed in a remote station. In accordance with yet another feature of the invention, the ring line includes two stations connected to the outputs of the probes. This is done in order to improve the reliability against failure. The ring line then preferably transmits the digitized values in time-multiplex. In addition, however, transmission of analog values as an alarm signal can be provided so that an indication is still obtained if the data conversion fails.

In accordance with yet a further feature of the invention, there are provided filters connected to the pickups for frequency selection.

In accordance with yet an added feature of the invention, there is provided a transmitter disposed at the vessel for a calibration signal.

In accordance with a concomitant feature of the invention, there is provided another transmitter for a test signal with a spatially defined position.

Other features which are considered as characteristic for the invention are set forth in the appended claims.

Although the invention is illustrated and described herein as embodied in a method for finding a leak in pressure-carrying vessels and apparatus for carrying out the method, it is nevertheless not intended to be limited to the details shown, since various modifications and structural changes may be made therein without departing from the spitit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1:
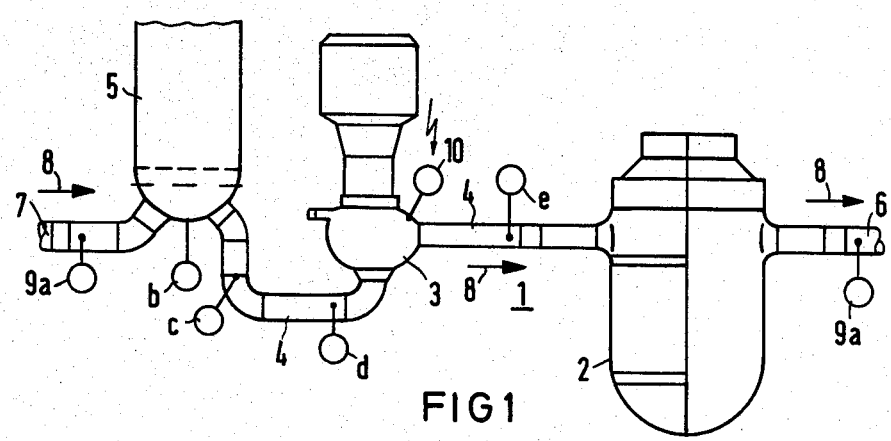
FIG. 1 is a fragmentary, diagrammatic, side-elevational view of a part of the primary loop of a pressurized-water reactor.

Referring now to the figures of the drawings in detail and first particularly to FIG. 1 thereof, there is seen a primary loop 1 of a pressurized-water reactor, including a reactor pressure vessel 2, in which a non-illustrated reactor core is housed. The core is cooled by pressurized water which is conducted by a reactor cooling pump 3 through pipelines 4 and a steam generator 5. The pressurized water heated up in the reactor core gives off its heat to feedwater which is correspondingly evaporated in the incompletely shown steam generator 5. The steam then drives a turbine for a generator.

The pump 3 is disposed in the so-called cold leg or line of the nuclear reactor, since the steam generator 5 is directly acted upon in the direction of the arrows 8 through the pipe ends 6 and 7. Contrary to the presentation in FIG. 1, the pipe ends 6, 7 are connected to each other. Five probes 9 which are designated with letters a to e, are disposed in the primary loop 1. The probes 9 are of identical construction. The probes include piezo-electric pickups which are connected to the wall of the primary loop 1 through a waveguide. The pickups are wideband pickups which are constructed for a frequency spectrum of 100 to 800 kHz. The waveguide is a metal rod, which may have a 4 mm diameter and a length of 30 mm. The waveguide is connected to the pickup through a conical end piece. The connection is established by a pressure pretension which simultaneously presses the waveguide against the wall or pipe wall of the primary loop 1.

An electroacoustic transmitter 10 is also attached to the primary loop 1, for furnishing a defined signal for the calibration which is introduced at a defined point, namely, at the housing of the main coolant pump 3.

Figure 2:
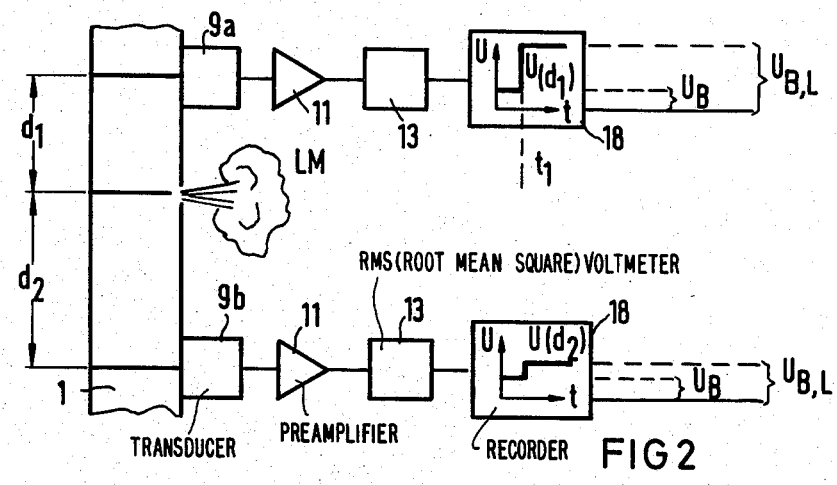
FIG. 2 is a block and schematic circuit diagram of the leak localizing device of FIG. 1.

FIG. 2 shows a diagrammatic and schematic view of the placement of two probes $9a$ and $9b$ on the wall of the reactor cooling loop 1. A leak L with a leakage rate M is indicated between the probes $9a$ and $9b$. The leak L is spaced from the probe $9a$ by a distance $d_1$ and from the probe $9b$ by a distance $d_2$. The probe spacing $d_1 + d_2$ is, for instance, 10 m. The outputs of the probes feed voltmeters 13 forming effective or r.m.s. values through preamplifiers 11. As indicated at reference numeral 18, the voltmeters 13 show a rise of the noise at the beginning of the leakage at the time $t_1$. The amount of increase of the noise, i.e., the r.m.s. value change of the voltmeters 13, depends on the distance from the leak to the pickups 9a, 9b because the noise arriving at the probes 9a, 9b is attenuated in the wall as sound conducted through solids or solid-conducted sound noise. The pickup 9a with the shorter distance $d_1$ furnishes a stronger signal $U(d_1)$ than the farther-removed pickup 9b with the signal $U(d_2)$.

In FIG. 2, the operational background of the leak noise, i.e., the noise level prevailing in normal operation, is designated with reference symbol $U_B$; the noise value $U_{B,L}$ occuring at $t_1$ with the start of the leak, is composed of the background noise $U_B$ and the additional noise stemming from the leak L.

Figure 3:
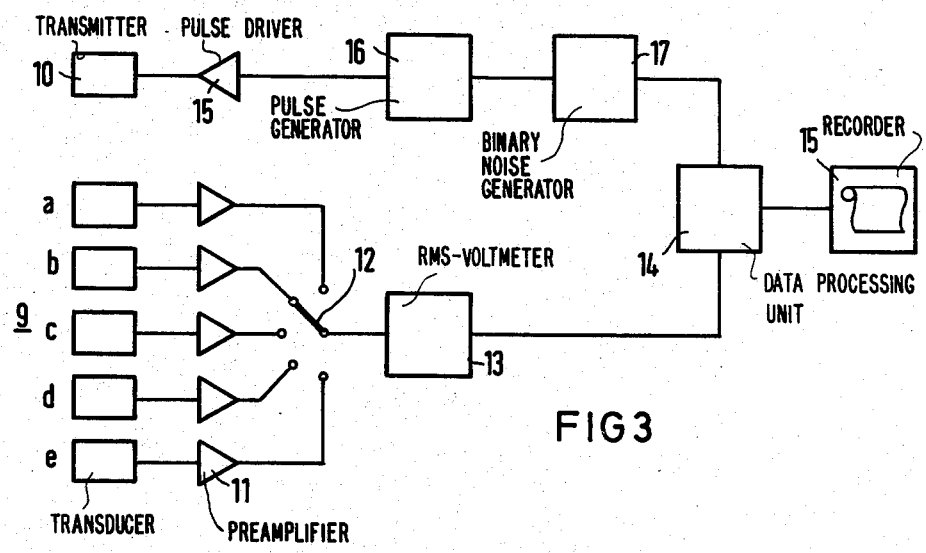
FIG. 3 is another block and schematic diagram including the essential elements of a device according to the invention.

FIG. 3 shows that the probes 9a to 9e are equipped with wideband amplifiers 11. The amplifiers 11 of the probes 9 are connected by a channel selector switch 12 to the r.m.s.-value voltmeter 13, the output of which is connected to a data processing system 14. The amplifier 15 of the transmitter 10 is connected through a pulse former 16 to a binary noise generator 17 which is addressed at certain times by the data processing system 14. The data processing system 14 has a recorder 15 at its output. The recorder 15 may also include a magnetic recording.

Figure 4:
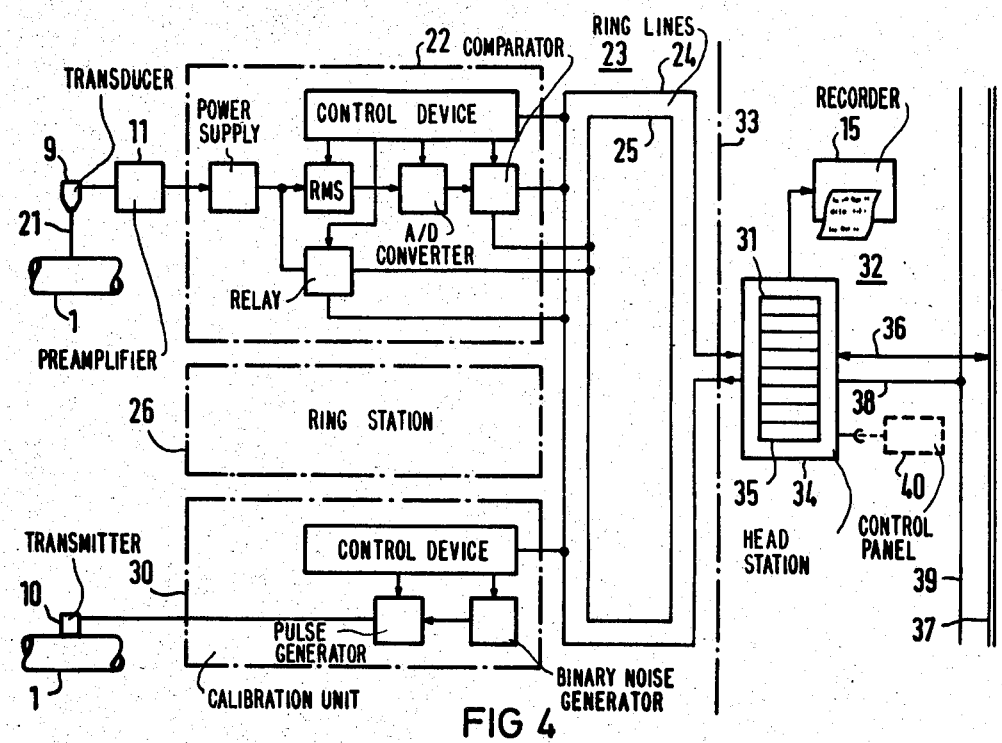
FIG. 4 is a more detailed schematic and diagrammatic presentation of the probes and evaluation devices used in the method according to the invention.

FIG. 4 illustrates in more detail that every probe 9 is connected through a waveguide 21 to the primary loop 1 which represents the vessel wall. The probe 9 is connected through an amplifier 11 having a gain of 40 dB to a module 22 indicated by a broken line. The module 22 includes control electronics, especially for the clocked sampling of the probe 9, an analog logic and a digitizing unit, the values of which are fed to a double ring line 23 with the ring lines 24 and 25. The ring line 23 is connected to every one of the probes 9, and optionally to a concentrator in which several probes 9 with their modules 22 are combined to form a ring station, as indicated at reference numeral 26.

The ring 24 of the ring line 23 is bipolar and serves for digital data transmission. The ring 25 transmits four analog signal values and two alarm values.

At least one calibrating unit 30 is also connected to the ring line 23. The unit 30 is connected to the transmitter 10 which is provided for issuing sound signals defined as to frequency and amplitude. However, with two physically spaced-apart transmitters 10, the localizing function can be even substantially more accurately checked.

The ring line 23 leads to a head station 32 which is outside the safety container that encloses the primary loop 1 and is indicated by the dot-dash line 33. The head station 32 includes digital evaluation electronics 34 with memories 35 and a microprocessor 31 which controls the recorder 15. The evaluation electronics 34 are connected through a line 36 to a bus 37 which leads to a diagnostic system. A line 38 leads to another bus 39 which is associated with the control mechanism of the nuclear power station that includes the pressurized-water reactor. A mobile operating panel 40 can be connected to the evaluation electronics.

For calibration, the measured values of all of the probes 9 which are obtained during the operation of the transmitter 10, are compared with each other. Because of the different distances d between the probes 9 and the transmitter 10, the measured values are different. A reference variable is formed from the measured values and the probes 9 are adjusted to the reference variable with a calibration factor.

Figure 5:
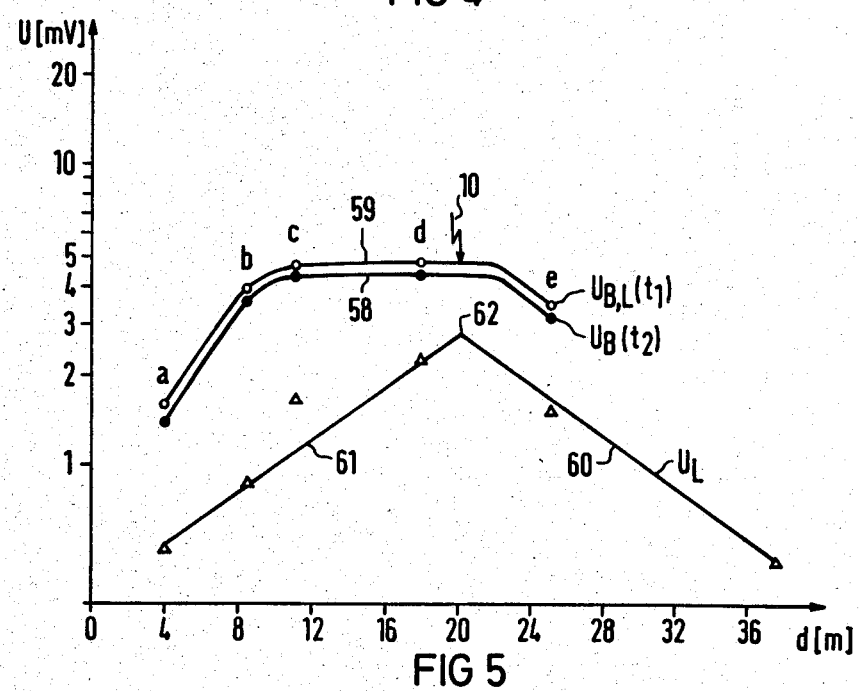
FIG. 5 is a graphical presentation of the measured values and their processing, for localizing a simulated leak noise such as is used for calibration.

FIG. 5 shows a diagram with r.m.s. values U in mV on the logarithmically divided ordinate, versus the distance d in m on the linearly divided abscissa, which indicates that the operating noises $U_B(t_2)$ in the five probes 9a to e furnish an r.m.s. value which is in the range between 1 and 5 mV of the output voltage, as is shown by the solid measuring points of a curve 58. For simulating a leak, a high-frequency signal such as would be generated in the event of a leak is imposed on the operating noise with the transmitter 10. This is used to obtain the higher measurement values $U_{B,L}(t_1)$ of the curve 59 indicated by the circles. The pure transmission signal $U_L = \sqrt{U_{B,L}^2 - U_B^2}$ is then obtained from the root of the difference of the squares of the measured values. This transmitter signal depends exponentially on the location and, in the semi-logarithmic plotting shown, furnishes two straight lines 60, 61 at an angle to each other. Their intersection 62 shows the location of the simulated leak L.

In case of an actual leak, corresponding straight lines 60, 61 are obtained for localizing the leak from the noises of the sound conducted through solids which are excited by the liquid escaping from the leak. The accuracy of the localization can be increased even further by multiple measurements at different frequencies because the attenuation of the noises of the sound conducted through solids used for localizing are frequency-dependent.

The foregoing is a description corresponding in substance to German Application No. P 33 36 245.9, filed Oct. 5, 1983, the International priority of which is being claimed for the instant application, and which is hereby made part of this application. Any material discrepancies between the foregoing specification and the aforementioned corresponding German application are to be resolved in favor of the latter.

We claim:

1. Method for determining the location of a leak in pressure-carrying vessels, including a plurality of probes spaced-apart on walls of the vessels for picking up high-frequency solid-conducted sound noises, and an amplifier connected to the probes, which comprises determining the solid-conducted sound noises by comparing with a background noise averaged over at lest ten minutes, forming an r.m.s. value in the amplifier from the sound noises, comparing the r.m.s. value with a threshold value, issuing a signal if the r.m.s. value exceeds the threshold value, comparing the solid-conducted sound noises from at least two probes with each other for localizing the leak, placing the r.m.s. value of the solid-conducted sound noises in a relationship relative to the spacing between the probes based on the comparison, and determining the location of the leak as the location of the maximum solid-conducted sound noise from the relationship.

2. Method according to claim 1, which comprises digitizing the solid-conducted sound noises for the comparison.

3. Method according to claim 1, which comprises interconnecting at least three probes through a ring line, and exciting two alarms through the ring line.

4. Method according to claim 1, which comprises comparing the comparison with a fixed upper threshold, a lower threshold and an upper sliding threshold.

5. Method according to claim 1, which comprises exciting the probes at defined time intervals with a given sound signal, and calibrating the probes by means of the excitation.

6. Method according to claim 5, which comprises exciting the calibrated probes with a spatially defined sound signal, and localizing the point of excitation.

7. Method according to claim 1, including a main coolant pump of a nuclear reactor connected to the vessels, which comprises shutting off the main coolant pump during the determination of the solid-conducted sound noises.

8. Method for determining the location of a leak in pressure-carrying vessels, including a plurality of probes spaced-apart on walls of the vessels for picking up high-frequency solid-conducted sound noises, and an amplifier connected to the probes, which comprises forming an r.m.s. value in the amplifier from the sound noises, comparing the r.m.s. value with a threshold value, issuing a signal if the r.m.s. value exceeds the threshold value, comparing the solid-conducted sound noises from at least two probes with each other for localizing the leak, carrying out the comparison separately for different frequencies, averaging the location determined by the separate comparisons, placing the r.m.s. value of the solid-conducted sound noises in a relationship relative to the spacing between the probes based on the comparison, and determining the location of the leak as the location of the maximum solid-conducted sound noise from the relationship.

9. Apparatus for determining the location of a leak in pressure-carrying vessels, comprising a plurality of probes with outputs including piezoelectric pickups spaced apart on walls of the vessels for picking up high-frequency solid-conducted sound noises, an amplifier connected to the probes for forming an r.m.s. value from the sound noises, a ring line interconnecting said outputs of said probes, and a head station connected to said ring line, said head station including at least one memory forming a long-term average.

10. Apparatus according to claim 9, wherein said ring line includes two stations connected to said outputs of said probes.

11. Apparatus according to claim 9, including filters connected to said pickups for frequency selection.

12. Apparatus according to claim 9, including a transmitter disposed at the vessel for a calibration signal.

13. Apparatus according to claim 12, including another transmitter for a test signal with a spatially defined position.

14. Apparatus for determining the location of a leak in pressure-carrying vessels, comprising a plurality of probes with outputs including piezoelectric pickups spaced apart on walls of the vessels for picking up high-frequency solid-conducted sound noises, an amplifier connected to the probes for forming an r.m.s. value from the sound noises, means connected to said amplifier for comparing the r.m.s. value with a threshold value and issuing a signal if the threshold value is exceeded by the r.m.s. value, means connected to said amplifier for comparing the solid-conducted sound noises from at least two probes with each other for localizing the leak, means connected to said comparing means for placing the r.m.s. values of the solid-conducted sound noises in a relationship relative to the spacing between said probes based on the comparison, means connected to said placing means for determining the location of the leak as the location of the maximum solid-conducted sound noise from the relationship, a ring line interconnecting said outputs of said probes, and a head station connected to said ring line, said head station including at least one memory forming a long-term average.

15. Apparatus according to claim 14, wherein said ring line includes two stations connected to said outputs of said probes.

16. Apparatus according to claim 14, including filters connected to said pickups for frequency selection.

17. Apparatus according to claim 14, including a transmitter disposed at the vessel for a calibration signal.

18. Apparatus according to claim 17, including another transmitter for a test signal with a spatially defined position.

* * * * *